(12) United States Patent
Garris

(10) Patent No.: US 7,695,639 B2
(45) Date of Patent: *Apr. 13, 2010

(54) CALCIUM HYPOCHLORITE COMPOSITIONS

(75) Inventor: John P. Garris, Suwanee, GA (US)

(73) Assignee: Bio-Lab, Inc.

( * ) Notice: Subject to any disclaimer, the term of this patent is extended or adjusted under 35 U.S.C. 154(b) by 0 days.

This patent is subject to a terminal disclaimer.

(21) Appl. No.: 12/049,913

(22) Filed: Mar. 17, 2008

(65) Prior Publication Data

US 2009/0008603 A1 Jan. 8, 2009

Related U.S. Application Data

(60) Division of application No. 11/757,722, filed on Jun. 4, 2007, now Pat. No. 7,364,669, which is a continuation of application No. 11/341,548, filed on Jan. 27, 2006, now abandoned, which is a continuation of application No. 10/872,202, filed on Jun. 18, 2004, now Pat. No. 7,045,077.

(51) Int. Cl.
C01B 11/06 (2006.01)
C11D 3/395 (2006.01)

(52) U.S. Cl. .............. 252/186.36; 252/186.37; 252/187.27; 252/187.28; 252/187.29; 252/187.3; 423/474

(58) Field of Classification Search ............ 252/186.36, 252/187.28
See application file for complete search history.

(56) References Cited

U.S. PATENT DOCUMENTS

| 3,793,216 | A | * | 2/1974 | Dychdala et al. | ....... 252/186.37 |
|---|---|---|---|---|---|
| 4,355,014 | A | * | 10/1982 | Murakami et al. | .......... 423/265 |
| 6,638,446 | B1 | * | 10/2003 | Mullins | ................. 252/187.28 |
| 7,045,077 | B2 | * | 5/2006 | Garris | ................... 252/186.36 |
| 7,364,669 | B2 | * | 4/2008 | Garris | ................... 252/186.36 |
| 2004/0197395 | A1 | * | 10/2004 | Brennan et al. | ............. 424/464 |
| 2007/0125979 | A1 | * | 6/2007 | Lei et al. | ..................... 252/176 |

* cited by examiner

Primary Examiner—Joseph D Anthony
(74) Attorney, Agent, or Firm—Katten Muchin Rosenman LLP

(57) ABSTRACT

Stable compositions of calcium hypochlorite containing selected hydrated inorganic salts having a sufficiently high enthalpy and the ability to provide water release to sufficiently quench reactions and reduce the potential for conflagration.

9 Claims, 3 Drawing Sheets

Figure 2   Reactions of Calcium Hypochlorite + Brake Fluid (Control) Compared to Calcium Hypochlorite Blends + Brake Fluid

CALCIUM HYPOCHLORITE COMPOSITIONS

This application is a divisional of co-pending U.S. application Ser. No. 11/757,722 filed Jun. 4, 2007, which is a continuation of U.S. application Ser. No. 11/341,548 filed Jan. 27, 2006, now abandoned, which is a continuation of U.S. application Ser. No. 10/872,202 filed Jun. 18, 2004, now issued as U.S. Pat. No. 7,045,077. Each of these patents and patent applications are incorporated herein by reference in its entirety.

FIELD OF THE INVENTION

The present invention relates generally to stable compositions of calcium hypochlorite, and more particularly compositions that have improved stability. In a further aspect, the present invention relates to a method of stabilizing calcium hypochlorite.

BACKGROUND OF THE INVENTION

Calcium hypochlorite (cal hypo) has been around for nearly 100 years. Initially, unrefined cal hypo, which was known as "bleaching powder", was produced containing about 35% available chlorine. In the 1930's, manufacturers succeeded in refining cal hypo; anhydrous cal hypo was produced containing 80% available chlorine or higher. After several fires, research was done that showed that cal hypo at 70% available chlorine was less vigorous than 80% available chlorine; therefore, manufacturers limited anhydrous cal hypo to 70% available chlorine.

Anhydrous calcium hypochlorite containing 70% available chlorine was involved in many shipboard fires that occurred during the late 1960's and early 1970's and caused major property damage and loss of life. Due to these incidences, the manufacturers of cal hypo produced less reactive hydrated forms of cal hypo. See, U.S. Pat. Nos. 3,544,267; 3,895,099 and 4,053,429. They also patented hydrated salts mixed with anhydrous cal hypo to form hydrated cal hypo. See, U.S. Pat. No. 3,793,216.

Hydrated calcium hypochlorite containing at least 65% available chlorine and from about 5.5 to 16% water are available as shown in *Chemical Economics Handbook, Hypochlorite Bleaches* (2003) SRI International. Those containing 5.5 to 10% moisture became the most widely available commercial form and designated by the United Nations as UN 2880. Even at 10% moisture, dihydrate cal hypo is not completely saturated with water; complete saturation would be approximately 17% water. Commercial cal hypo is lower in water than saturation because higher water content would have an adverse effect on the stability of cal hypo. The loss of stability of the available chlorine in cal hypo due to the presence of moisture content, temperature and humidity is well known in the art; see, U.S. Pat. Nos. 3,544,267, 4,355,014 and 4,965,016, and Bibby and Milestone, *J. Chem. Tech. Biotechnol* (34A), pp. 423-430 (1984).

The commercialization of hydrated cal hypo in addition to changes in storage of the material aboard ships proposed by Clancey, *Journal of Hazardous Materials*, (1) pp. 83-94, (1975/76) made cal hypo safer in marine transport. This was seemingly confirmed by the work of Mandell, *Fire Technology* (7), pp. 157-161 (1971), that showed an endotherm for hydrated cal hypo at 40° C. according to *Differential Scanning Calorimetry* (DSC). This endotherm, which is not present in the anhydrous material, is thought to provide a heatsink to quench an exotherm so that no propagation occurs. This investigation also used tests incorporating lit matches, lit cigarettes, or one drop of glycerin as an ignition source for the calcium hypochlorite.

A study by Cardillo, *Rev. Combust*, (48) pp. 300-305 (1994), concluded that the addition of moisture lowers the temperature at which exothermic decomposition of cal hypo takes place. They also concluded that the heat generated during the decomposition would be increased. Gray and Halliburton, *Fire Safety Journal* (35), pp. 223-239 (2000), investigated hydrated cal hypo based on marine fires that happened in the late 1990's. They concluded that hydrated cal hypo had a lower critical ambient temperature for large quantities of material than was previously thought. Both studies confirm that hydrated cal hypo is not as stable to exothermic decomposition than was previously reported. The UN Transport of Dangerous Goods (TDG) subcommittee confirmed this using a self-accelerating decomposition test (SADT) on various manufactured cal hypos. See, UN/SCETDG/21/INF.8 (2002).

While improving the available chlorine and reducing reactivity of cal hypo has been going on for a long time, another difficulty using cal hypo, namely, the formation of calcium scale, has been equally investigated. Since the earliest use of cal hypo as a liquid bleaching compound, scale, such as calcium carbonate, has been an issue. Scale inhibitors such as sodium pyrophosphate, sodium tripolyphosphate, sodium polyacrylate, phosphonobutane tricarboxylic acid and alkali salts of PESA and/or polymaleic acid have been added to improve the clarity of cal hypo solutions or prevent the deposition of calcium sensitive soaps and detergents or reduce scaling in equipment feeding cal hypo. Mullins, in U.S. Pat. No. 5,112,521 and Faust, U.S. Pat. No. 3,669,894, also confirm what is known to those skilled in the art; it is difficult to find additives that can be admixed with cal hypo since those additives can affect stability of the cal hypo causing a loss of available chlorine especially at elevated temperatures.

Investigators have added materials that reduced dusting and increased the resistance to ignition by lit cigarettes, matches, or a drop of glycerin using spray-grained low melting hydrated inorganic salts such as: magnesium sulfate hydrates, sodium tetraborate hydrates, aluminum sulfate hydrates, and sodium phosphate hydrates; see, U.S. Pat. No. 4,146,676. Additionally, coatings of alkaline metal salts like sodium chloride and alkaline materials like calcium hydroxide may also be used to buffer compositions above pH 9. Both '676 and Pickens, WO 99/61376, agree that the presence of acidic material causes a decrease in storage stability.

Other investigators have added materials to calcium hypochlorite to provide other functions. For water treatment, Loehr, U.S. Pat. No. 4,747,978, added 0.1 to about 3% water soluble aluminum salts to increase water clarity. Pickens added hydrated aluminum salts as long as they were neutralized with an equivalent amount of hydrated borate salt. Girvan, U.S. Pat. No. 5,676,844, added hydrated borate salts or boric acid to improve the properties of cal hypo. Robson in U.S. Pat. No. 3,560,396 used spray-dried sodium nitrate preparations of cal hypo to reduce reactivity.

Only two inventive compositions containing admixed formulations with calcium hypochlorite disclose increased stability to loss of available chlorine. Jaszka, U.S. Pat. No. 3,036,013, adds a solution of a soluble salt that would react with the calcium hypochlorite to form an insoluble calcium salt at the surface of each granule. This coating would increase the stability of the particle in the presence of humidity and moisture. The coating would also slow the dissolution rate of the composition. Suitable salts include sodium silicate, sodium borate, sodium carbonate, trisodium phosphate, disodium phosphate and potassium fluoride. The composition of Murakami, in U.S. Pat. No. 4,355,014, used at least 5% calcium hydroxide to increase the stability of compositions containing at least 4% and up to 22% moisture. In both cases, the process and/or the material added result in slowing down the dissolving rate of the cal hypo. This is not a desirable effect when adding the material as a dry granular blend in a water treatment application or other applications that needs a quick dose of free available chlorine.

In response to marine fires and retail store fires that occurred during the 1990's, cal hypo manufactures and marketers continued to investigate making cal hypo safer. Girvan promoted the composition in U.S. Pat. No. 5,676,844 as less reactive based on the results of U.S. Pat. No. 3,793,216, as well as the algicidal and fungicidal benefits of the composition.

U.S. Pat. No. 6,638,446 uses the UN DOT Oxidizer test to classify their material, which contains magnesium sulfate heptahydrate as a non-oxidizer. This is also the claim by Pickens in WO 99/61376. This test, which is used to classify materials as oxidizers, has come under scrutiny due to variability based on relative humidity, cellulose source, and ignition wire composition and diameter; see, *Journal of Loss Prevention in the Process Industries* (14), pp. 431-434, (2001) and *Journal of Safety and Environment* (2), pp. 32-35, (2002). Since cellulose is hygroscopic, the hydrated water could interfere with the results of this test. The '446 patent teaches away from other past tests using a lit cigarette, a lit match, or one drop of glycerin since none of these tests is demanding due to the absence of fuel. A better test is one that is more severe and also more reproducible than the UN/DOT oxidizer test.

Reactivity in compositions shown in U.S. Pat. No. 3,793, 216, using one drop of glycerin were noted by a time delay in reactions as well as the reaction itself and the amount of destruction to the sample. Glycerin as well as brake fluid are especially reactive with calcium hypochlorite. The reaction with brake fluid has been detailed chemically; see, *Journal of Forensic Sciences* (36), pp. 902-907, (1991). This exothermic chemical reaction initially has a delay period until a fireball erupts; the fireball lasts a few seconds and consumes all the brake fluid and much or all of the calcium hypochlorite depending on the quantity of materials used. The "freshness" of the cal hypo is also a factor in the reaction.

The rationale for changing anhydrous calcium hypochlorite to hydrated calcium hypochlorite was to make the product safer due to decomposition by a cigarette, spark, or one drop of contamination by an organic compound. The addition of water to anhydrous cal hypo changed the characteristics of the material including a unique hazardous chemical designation of UN 2880; however, hydrated cal hypo is still a highly reactive material that can be purchased by a consumer. Unsuspecting consumers are not keenly aware of the potential danger the material poses. Thus the need exists to make a calcium hypochlorite containing formulation that provides to the consumer a product that is safe to transport, store, and use. Accordingly, there is a need to improve the safety of calcium hypochlorite formulations to provide a stable, safe, fast dissolving and functional blend for water treatment and other applications.

SUMMARY OF THE INVENTION

There is a need for a stable, safer, rapidly dissolving and multifunctional calcium hypochlorite formulation that can rapidly provide free available chlorine to water treatment and other applications. The present invention provides a solution for these needs.

BRIEF DESCRIPTION OF DRAWINGS

The present invention will be further understood with reference to the accompanying drawings, wherein.

DESCRIPTION OF THE PREFERRED EMBODIMENT

Figure 1:
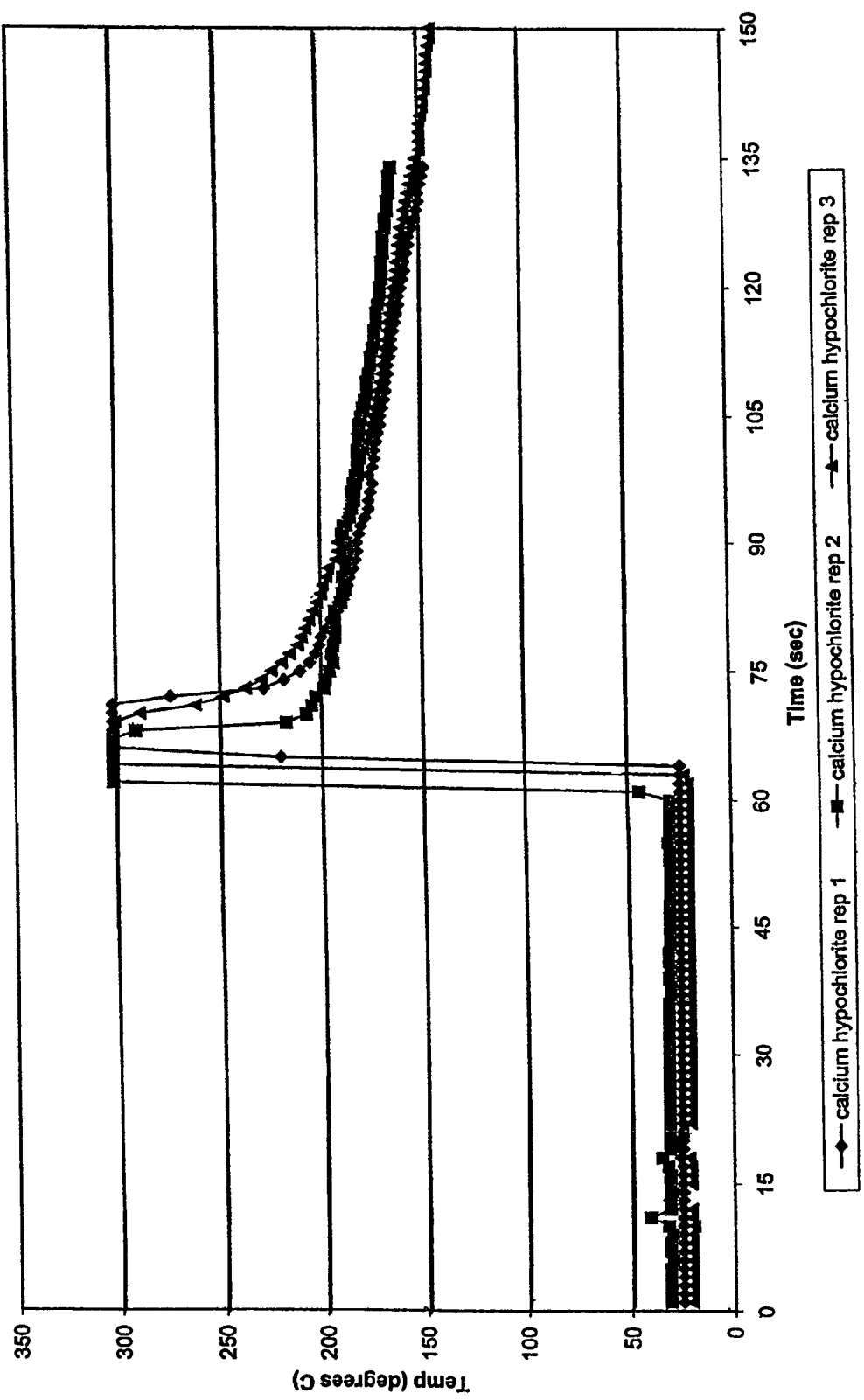
FIG. 1 is a chart of temperature over time of 3 Replicate Calcium Hypochlorite and Brake Fluid Reaction.

For the purpose of providing a further understanding of the principles of the invention, reference will now be made to the preferred embodiments of the present invention. Specific language will be used to describe the same; nevertheless, it will be understood that no limitation of the scope of the invention is thereby intended.

Many hydrated salts and other chemicals can produce endothermic reactions upon heating; see WO 99/11455. For hydrated salts, the endothermic reaction generally occurs as part of a phase transition (i.e. solid to liquid) so the endotherm occurs when water is released. Phase transitions occur at different temperatures for various compounds. For simplification purposes, melting point is used herein as the phase transition point. The phase transition for a given salt may be below ambient temperature (i.e. dipotassium phosphate hexahydrate) or above the boiling point of water (i.e. magnesium chloride hexahydrate). See, *Thermochemica Acta* (67), pp. 167-179 (1983). When this endothermic reaction occurs is critical for the proper release of water for a given application.

The amount of heat energy absorbed varies for various hydrated compounds. Attributes like percent weight water or the sheer number of hydrated waters are not good measures of how much heat energy can be absorbed. Enthalpy, $\Delta H$, is the best means by which to measure the heat energy absorbed; however, most measurements are made using moles of material. From a formulation perspective, weight is a more common means to measure materials thus, the use should be optimized on a weight basis. For both of these chemical properties, Table 1 was generated using various references: *CRC Handbook of Chemistry and Physics*, 80$^{th}$ Edition (1999), D. R. Lide; *CRC Handbook of Chemistry and Physics*, 52$^{nd}$ Edition (1971), R. Weast; *The Merck Index*, 13$^{th}$ Edition (2001), M. J. O'Neil, et al.; and *Selected Values of Chemical Thermodynamic Properties* (1952), F. D. Rossini, et al. Table 1 is an extensive list, but not an exhaustive list. Although pure hydrated inorganic salts and double salts are referenced here, the present invention also contemplates other more complex hydrated salts.

TABLE 1

| Salt | melting point °C. | water of hydration | $\Delta Hf$ kcal/mol | molecular weight | $\Delta H$ cal/gram | Percent water |
| --- | --- | --- | --- | --- | --- | --- |
| aluminum chloride | 100 | 6 | −641.1 | 241.4 | 530.6 | 44.8 |
| magnesium chloride | 117 | 6 | −597.4 | 203.3 | 478.2 | 53.2 |
| lithium selenide | n/a | 9 | −729.0 | 255.0 | 461.6 | 63.6 |
| sodium carbonate | 33-35 | 10 | −975.6 | 286.1 | 444.9 | 63.0 |
| lithium chloride | n/a | 3 | −313.5 | 96.4 | 439.9 | 56.1 |

TABLE 1-continued

| Salt | melting point ° C. | water of hydration | ΔHf kcal/mol | molecular weight | ΔH cal/gram | Percent water |
|---|---|---|---|---|---|---|
| sodium hydrogen phosphate | 37 | 12 | −1266.4 | 358.1 | 433.9 | 60.4 |
| sodium metasilicate | 40-48 | 9 | −1002.0 | 284.2 | 418.0 | 57.1 |
| strontium hydroxide | 100 | 8 | −801.2 | 265.8 | 412.0 | 54.2 |
| trisodium phosphate | ~75 | 12 | −1309.0 | 380.1 | 408.8 | 56.9 |
| potassium fluoride | 19.3 | 4 | −418.0 | 130.1 | 402.2 | 55.4 |
| magnesium sulfate | 150 | 7 | −808.7 | 246.5 | 400.0 | 51.2 |
| calcium chloride | 30 | 6 | −623.2 | 219.0 | 394.3 | 49.4 |
| sodium sulfate | 32.4 | 10 | −1033.5 | 322.2 | 386.7 | 55.9 |
| aluminum sulfate | 86 | 18 | −2118.5 | 666.4 | 385.8 | 48.7 |
| sodium tetraborate | ~75 | 10 | −1497.2 | 381.4 | 371.0 | 47.3 |
| magnesium sulfate | 70-80 | 6 | −736.6 | 228.5 | 369.0 | 47.3 |
| magnesium bromide | 165 | 6 | −575.4 | 292.2 | 359.0 | 37.0 |
| rubidium aluminum sulfate | 99 | 12 | −1448.0 | 520.8 | 356.0 | 41.5 |
| barium hydroxide | 78 | 8 | −799.5 | 315.5 | 351.5 | 45.7 |
| potassium aluminum sulfate | 80-92.5 | 12 | −1447.7 | 474.4 | 347.6 | 45.6 |
| magnesium nitrate | 89 | 6 | −624.4 | 256.4 | 346.5 | 42.2 |
| sodium hydrogen phosphate | 48.1 | 7 | −913.3 | 268.1 | 340.6 | 47.1 |
| nickel sulfate | 31.5 | 7 | −712.9 | 280.9 | 339.3 | 44.9 |
| zinc sulfate | 100 | 7 | −735.1 | 287.5 | 336.0 | 43.9 |
| beryllium sulfate | ~100 | 4 | −576.3 | 177.1 | 333.6 | 40.7 |
| lithium nitrate | 29.9 | 3 | −328.6 | 123.0 | 324.6 | 44.0 |
| strontium chloride | ~60 | 6 | −627.1 | 266.6 | 308.7 | 40.6 |
| zinc nitrate | 36.4 | 6 | −550.9 | 297.5 | 299.2 | 36.3 |
| sodium pyrophosphate | 76.3 | 10 | −1468.2 | 446.1 | 290.1 | 40.4 |
| calcium bromide | 38 | 6 | −597.2 | 308.0 | 289.3 | 35.1 |
| copper sulfate | 110 | 5 | −544.5 | 249.7 | 286.2 | 36.1 |
| copper nitrate | 24.4 | 6 | −504.3 | 295.6 | 284.5 | 36.6 |
| aluminum nitrate | 73 | 9 | −897.3 | 375.1 | 275.9 | 43.2 |
| sodium tetraborate | 120 | 5 | −1143.5 | 291.3 | 263.7 | 30.9 |
| silver fluoride | n/a | 4 | −331.5 | 198.9 | 260.5 | 36.2 |
| calcium iodide | n/a | 8 | −700.7 | 437.9 | 252.4 | 32.9 |
| lithium bromide | 44 | 2 | −229.9 | 122.3 | 250.4 | 29.5 |
| lithium iodide | 73 | 3 | −285.0 | 187.9 | 249.2 | 28.8 |
| strontium bromide | 88 | 6 | −604.4 | 355.5 | 243.3 | 30.4 |
| calcium nitrate | ~40 | 4 | −509.4 | 236.2 | 229.4 | 30.5 |
| strontium iodide | 90 | 6 | −571.2 | 449.5 | 197.8 | 24.1 |
| sodium bromide | 36 | 2 | −227.3 | 138.9 | 184.4 | 25.9 |
| strontium nitrate | 100 | 4 | −514.5 | 283.7 | 176.4 | 25.4 | n/a—not available

For application to calcium hypochlorite, when water is released from a salt hydrate is important. If water is released too easily, the water may easily transfer to the calcium hypochlorite thus reducing chlorine stability. If water is not released quickly enough, the decomposition of cal hypo may overwhelm the system during a conflagration. The present invention provides blends of at least two hydrated salts with calcium hypochlorite that provide water release to sufficiently quench reactions and reduce the potential for a conflagration while providing increased chlorine stability as compared to blends that are currently available. Inventive blends with other endothermic compounds and cal hypo are also disclosed herein. Additionally, the blends of the current invention provide added benefits to users by incorporating other water treatment functions for various applications of the inventive compositions.

As previously indicated, hydrated calcium hypochlorite is the preferred sanitizer used in the present invention. In the preferred embodiments, hydrated calcium hypochlorite contains at least 55% available chlorine, and more preferably at least 65% available chlorine. Hydrated cal hypo ideally contains from 5% to 22% water, and more preferably, the hydrated calcium hypochlorite contains about 5.5% to 10% water.

The concentration of the hydrated calcium hypochlorite compositions of the present invention is between about 40% and 90% by weight. Preferably, the compositions of the present invention contain between about 50% and 85% hydrated calcium hypochlorite. Most preferably, the compositions of the present invention contain about 60% to 80% hydrated calcium hypochlorite.

In the preferred embodiment of the invention, the hydrated salt has a phase transition temperature, as defined by melting point, between 19° C. and 200° C., and more preferably between 45° C. and 90° C. The pure, double or complex hydrated salt is an inorganic hydrated salt of fluoride, chloride, bromide, iodide, selenide, hydroxide, oxide, phosphate, silicate, borate, carbonate, nitrate and/or sulfate.

The preferred hydrated inorganic salts exhibit an enthalpy expressed in calories/gram of at least 150, more preferably at least 250 calories/gram.

Inorganic salt hydrates that meet these enthalpy and melting point criteria are the hydrates of aluminum chloride, magnesium chloride, lithium selenide, sodium carbonate, lithium chloride, sodium hydrogen phosphate, sodium metasilicate, strontium hydroxide, trisodium phosphate, potassium fluoride, magnesium sulfate, calcium chloride, sodium sulfate, aluminum sulfate, sodium tetraborate, magnesium sulfate, magnesium bromide, rubidium aluminum sulfate, barium hydroxide, potassium aluminum sulfate, magnesium nitrate, sodium hydrogen phosphate, nickel sulfate, zinc sulfate, beryllium sulfate, lithium nitrate, strontium chloride, zinc nitrate, sodium pyrophosphate, calcium bromide, copper sulfate, copper nitrate, aluminum nitrate, sodium tetraborate, silver fluoride, calcium iodide, lithium bromide, lithium iodide, strontium bromide, calcium nitrate, strontium iodide, sodium bromide, and strontium nitrate. Representative hydrates are shown in the above Table 1.

Preferred compositions of the present invention include a composition of reduced potential for conflagration comprising hydrated calcium hypochlorite and at least two members selected from the group consisting of magnesium sulfate heptahydrate, potassium aluminum sulfate dodecahydrate, trisodium phosphate dodecahydrate, sodium tripolyphosphate hexahydrate and sodium tetraborate decahydrate.

More particularly a preferred composition of the present invention is a composition of reduced potential for conflagration comprising hydrated calcium hypochlorite, sodium tripolyphosphate hexahydrate, magnesium sulfate heptahydrate, potassium aluminum sulfate dodecahydrate and trisodium phosphate dodecahydrate.

Still more particularly a more preferred composition of the present invention is a composition which comprises about 40 to about 90% hydrated calcium hypochlorite, 0.1 to 19% magnesium sulfate heptahydrate, 0.1 to 19% potassium aluminum sulfate dodecahydrate, 0.1 to 19% trisodium phosphate dodecahydrate and 0.1 to 10% sodium tripolyphosphate hexahydrate.

According to another aspect of the invention, there are provided additive compositions for imparting reduced tendency for conflagration of a calcium hypochlorite blended with sodium tripolyphosphate hexahydrate, comprising at least one member selected from the group consisting of magnesium sulfate heptahydrate, potassium aluminum sulfate dodecahydrate, trisodium phosphate dodecahydrate and sodium tetraborate decahydrate.

In a still further aspect of the present invention, there is provided a method wherein there is added to the calcium hypochlorite a blend which comprises 40 to about 90% hydrated calcium hypochlorite, 0.1 to 19% magnesium sulfate heptahydrate, 0.1 to 19% potassium aluminum sulfate dodecahydrate, 0.1 to 19% trisodium phosphate dodecahydrate 0.1 to 10% sodium tripolyphosphate hexahydrate, and 0.1 to 10% sodium tetraborate decahydrate and 0.1 to 10% sodium tetraborate dodecahydrate.

The sanitizing compositions of the present invention are preferably solid granulated products of any size or shape above 150 microns in diameter. Granular cal hypo sanitizing compositions are preferred over powder cal hypo sanitizing compositions because of inhalation hazards inherent to powders (respirable powders are particles or particle agglomerates less than about 10 microns in diameter). The granular sanitizing compositions of the present invention are prepared by any known static or in-process mixing or blending technology such as a V-blender, ribbon blender, screw feeders, and the like. Alternatively, dry particle-size enlargement methods, preferably co-compaction or granulation may be used to compact inventive mixtures from powder blends into granules.

Additional components such as scale inhibitors, water clarifiers, anti-caking agents, humectants, binders, bulking agents, mold release agents, corrosion inhibitors, surfactants, glidants, or dyes may be incorporated into compositions of the present invention. The selection of such components is within the capability of those skilled in the art.

Compositions of the present invention are preferably used to treat recirculating water systems like swimming pools, spas, hot tubs, toilet bowls, reflecting pools, industrial water systems, fountains, etc. The present invention will sanitize, clarify, and reduce algae occurrence in water systems by contacting an effective amount of the sanitizing composition of the present invention with the water system through an appropriate application method. The methods of application may be manual or automatic.

Reference will now be made to specific examples. It is to be understood that the examples are provided to more completely describe preferred embodiments, and no limitation to the scope of the invention is intended thereby.

EXAMPLE 1

FIG. 1 shows the predictability of a single batch of calcium hypochlorite reacting with brake fluid. As described earlier, calcium hypochlorite reacts violently with Dot 3 brake fluid (Prestone) in a free radical depolymerization reaction of polyethylene glycol ether. The reaction of 50 grams of calcium hypochlorite and 10 milliliters (mls) of brake fluid is predictable for a given batch of calcium hypochlorite. Variations may occur with the reaction from different batches of cal hypo based on the attributes of the batch of calcium hypochlorite, such as age, moisture content and particle size.

The temperature measurement made in FIG. 1 was made with an IR thermometer with data acquisition software (Fisher Scientific). The temperature maximum of the thermometer is 300 degrees Celsius (C). This maximum temperature is exceeded for the time period when the curve is flat at 300° C.

Figure 2:
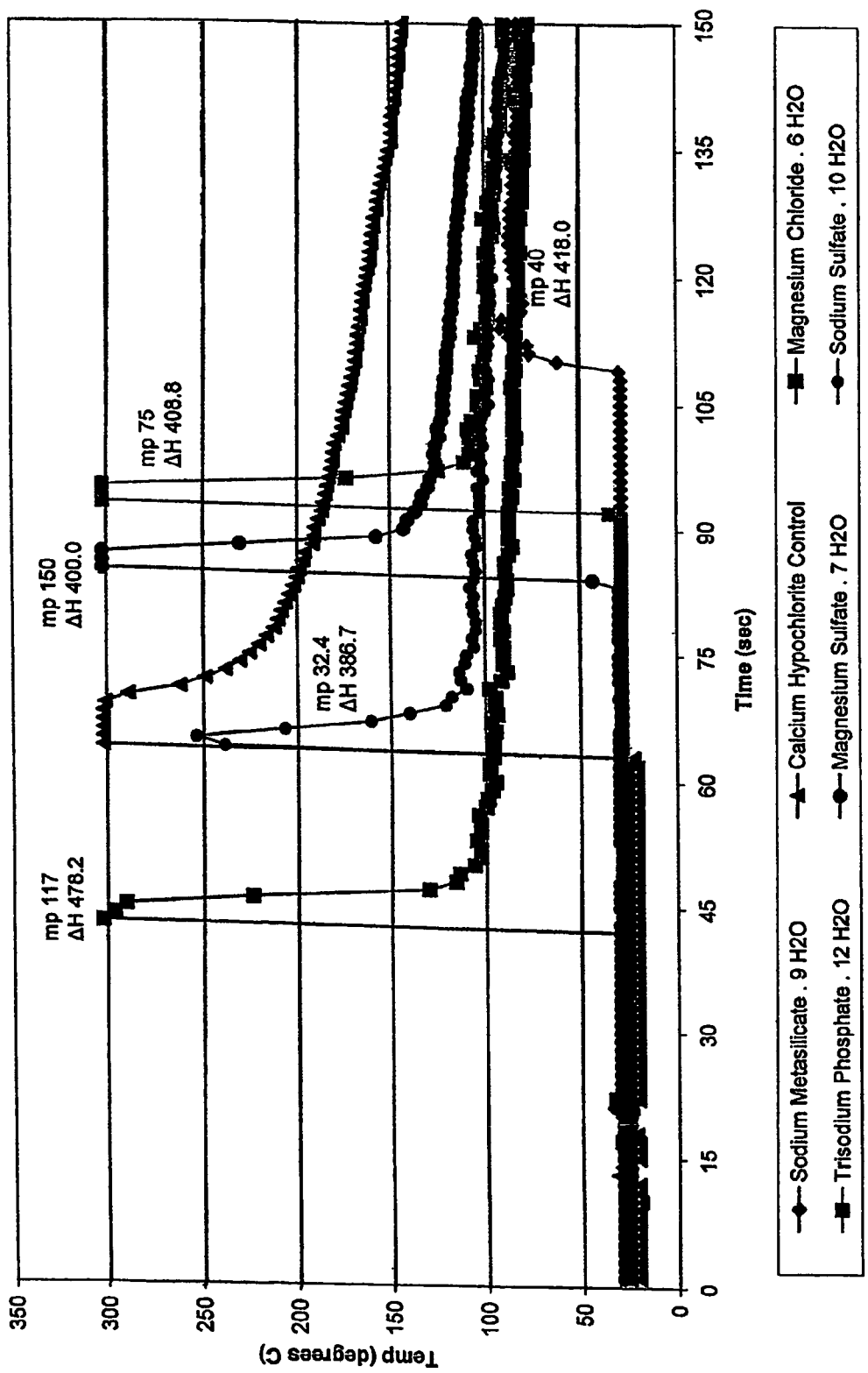
FIG. 2 is a chart of temperature over time for Reactions of Calcium Hypochlorite and Brake Fluid (Control) Compared to Calcium Hypochlorite Blends and Brake Fluid.

FIG. 2 shows the reaction of mixtures of various hydrated compounds blended with calcium hypochlorite. The blends contain 15 grams of the hydrated material and 35 grams of calcium hypochlorite. These are compared to a control containing 50 grams of calcium hypochlorite. The enthalpy (ΔH) and melting point (mp) are attributes of each compound that change the reaction curve. Potential interactions by each compound with calcium hypochlorite may also cause changes to the reaction curve as well as product stability.

FIG. 2 clearly shows that a low melting point is clearly the most important factor in reducing the reaction as shown by the reduced temperature output of sodium sulfate decahydrate (mp 32.4° C.) and sodium metasilicate nonahydrate (mp 40° C.). It is also clear that the enthalpy is also critical since the reaction with sodium sulfate decahydrate is substantially reduced (ΔH=386.7 calories/gram); however, the reaction with sodium metasilicate nonahydrate (ΔH=418.0 calories/gram) provides nearly total quenching of the reaction.

EXAMPLE 2

Reducing the reactivity of calcium hypochlorite is only one aspect of the current invention. Few additives are even compatible with cal hypo. The inventive mixtures herein are also stable providing high available chlorine even after being subjected to conditions that have a degrading effect on the available chlorine present in calcium hypochlorite. Other aspects of the invention will also be made known.

As described earlier, cal hypo degrades over time. This is accelerated by the presence of heat and moisture. Inventive mixtures were stored at 40 degrees C. under ambient humidity conditions in a convection oven. These conditions would be indicative of potential warehouse and transport conditions for the material. Table 2 shows the increased chlorine stability of the inventive formulations.

Each 200 gram sample contained 70% (47% available chlorine) calcium hypochlorite, 2% Sodium tripolyphosphate hexahydrate, and the balance of the composition as shown below. The formulation components are magnesium sulfate heptahydrate ($MgSO_4 \cdot 7H_2O$), trisodium phosphate dodecahydrate (TSP.12 $H_2O$), sodium tetraborate decahydrate (Borax.10 $H_2O$), and potassium aluminum sulfate dodecahydrate (K-Alum.12$H_2O$).

TABLE 2

| MgSO4 7H2O | TSP 12H2O | Borax 10H2O | K-Alum 12H2O | Days in Storage | Storage Temp ° C. | Material Consistency | Percent Available Chlorine |
|---|---|---|---|---|---|---|---|
| 28.0% | — | — | — | 56 | 40 | Dry | 28.3 |
| — | 28.0% | — | — | 61 | 40 | Dry | 28.3 |
| — | — | 28.0% | — | 63 | 40 | Dry | 22.3 |
| — | — | — | 28.0% | 60 | 40 | Moist | 30.7 |
| 7.0% | 7.0% | 7.0% | 7.0% | 62 | 40 | Dry | 38.2 |
| 9.3% | 9.3% | — | 9.3% | 61 | 40 | Dry | 42.7 |
| 9.3% | 18.7% | — | — | 56 | 40 | Dry | 35.5 |
| — | 9.3% | — | 18.7% | 55 | 40 | Dry | 38.1 |
| — | 18.7% | — | 9.3% | 59 | 40 | Dry | 33.7 |
| 9.3% | — | 9.3% | 9.3% | 55 | 40 | Dry | 32.5 |
| 3.5% | 17.5% | 3.5% | 3.5% | 61 | 40 | Dry | 37.9 |
| 3.5% | 3.5% | 3.5% | 17.5% | 60 | 40 | Moist | 37.4 |
| 3.5% | 3.5% | 17.5% | 3.5% | 54 | 40 | Dry | 18.8 |

The experiment above showed that trisodium phosphate dodecahydrate seemed to have appositive effect on chlorine stability and sodium tetraborate decahydrate seemed to have a negative effect on stability at higher levels. Potassium aluminum sulfate dodecahydrate in high amounts did not have a negative effect on chlorine stability but did make the samples moist which is not acceptable for a commercial product.

EXAMPLE 3

Based on the results of Example 2, a simplified experiment on material consistency and product flowability was performed. Sodium tetraborate decahydrate was removed from the experiment. The 200 gram samples were composed of a fixed amount of potassium aluminum sulfate at a nominal concentration of 9% to provide benefits to the pool water while minimizing the effect on product flowability. The formulation contained 2% sodium tripolyphosphate hexahydrate and 70% calcium hypochlorite. Magnesium sulfate heptahydrate and trisodium phosphate dodecahydrate were formulated in different percentages to make up the final 19% of the formula. A control containing straight calcium hypochlorite was used as a base for comparison of flowability results. Samples were stored in a convection oven at 50° C. for 6 days under ambient humidity conditions. This temperature is indicative of possible short-term transport and storage conditions that a product may be exposed to. The results are shown in Table 3.

The calcium hypochlorite control material was a free-flowing granular material after exposure to the test conditions. The only sample that was equal to cal hypo in material consistency and flowability was the sample containing 14.3% magnesium sulfate heptahydrate and 4.7% trisodium phosphate dodecahydrate. The samples containing 19% magnesium sulfate heptahydrate were slightly moist with granules adhering to each other and the container sides. The samples containing 19% trisodium phosphate dodecahydrate were dry and caked with significant effort needed to break granular masses. The samples containing 4.7% and 14.3%, and 9.5% of each magnesium sulfate heptahydrate and trisodium phosphate dodecahydrate, respectively, were free flowing after tapping the sample container.

EXAMPLE 4

Various 800 gram samples of different formulations were weighed, blended and packaged in high density polyethylene (HDPE) commercial packaging. These larger scale mixtures in commercial packaging were made to test stability, material consistency and flowability as well as pH. The mixtures began with 70% (47% available chlorine) calcium hypochlorite hydrated, 2% sodium tripolyphosphate hexahydrate, and the balance of 28% contained mixtures of magnesium sulfate heptahydrate, trisodium phosphate dodecahydrate, and potassium aluminum sulfate dodecahydrate. These samples were stored at 40° C. in a convection oven and ambient humidity conditions for a period of more than 3 months. The results are shown in Table 4.

TABLE 3

| MgSO4 7H2O | TSP 12H2O | Days in Storage | Storage Temp ° C. | Flowability Grade | Material Consistency | Flowability Description |
|---|---|---|---|---|---|---|
| Control | | 6 | 50 | 10 | Dry | Free flowing granules |
| 19.0% | — | 6 | 50 | 9 | Slightly moist | Slight granule caking |
| — | 19.0% | 6 | 50 | 2 | Dry | Dry caked granules |
| 14.3% | 4.7% | 6 | 50 | 10 | Dry | Free flowing granules |
| 4.7% | 14.3% | 6 | 50 | 6 | Dry | Free flowing after tapping container |
| 9.5% | 9.5% | 6 | 50 | 6 | Dry | Free flowing after tapping container |

TABLE 4

| MgSO4 7H2O | TSP 12H2O | K-Alum 12H2O | Days in Storage | Storage Temp ° C. | Material Consistency | Percent Available Chlorine | pH |
|---|---|---|---|---|---|---|---|
| 28.0% | — | — | 110 | 40 | Slightly Moist | 27.3 | 10.1 |
| — | 28.0% | — | 110 | 40 | Slightly Moist | 19.2 | 11.1 |
| — | — | 28.0% | 110 | 40 | Very Moist | 27.5 | 8.1 |
| 14.0% | 14.0% | — | 110 | 40 | Dry | 34.8 | 10.4 |
| — | 14.0% | 14.0% | 110 | 40 | Dry | 36.1 | 9.1 |
| 14.0% | — | 14.0% | 110 | 40 | Moist | 20.0 | 8.3 |
| 9.3% | 9.3% | 9.3% | 110 | 40 | Dry | 34.5 | 9.0 |

The results of Example 4 definitively show a synergistic effect that trisodium phosphate dodecahydrate has on the stability and material consistency of cal hypo formulas that contain either magnesium sulfate heptahydrate or potassium aluminum sulfate or both materials. These stable formulas also have a pH as low as 9.0. As stated earlier by those skilled in the art acidic materials added to calcium hypochlorite make cal hypo unstable. A pH closer to neutral is an advantage in many water treatment applications especially swimming pools and spas since chlorine efficacy and swimmer comfort is optimized at pH 7.5.

EXAMPLE 5

Figure 3:
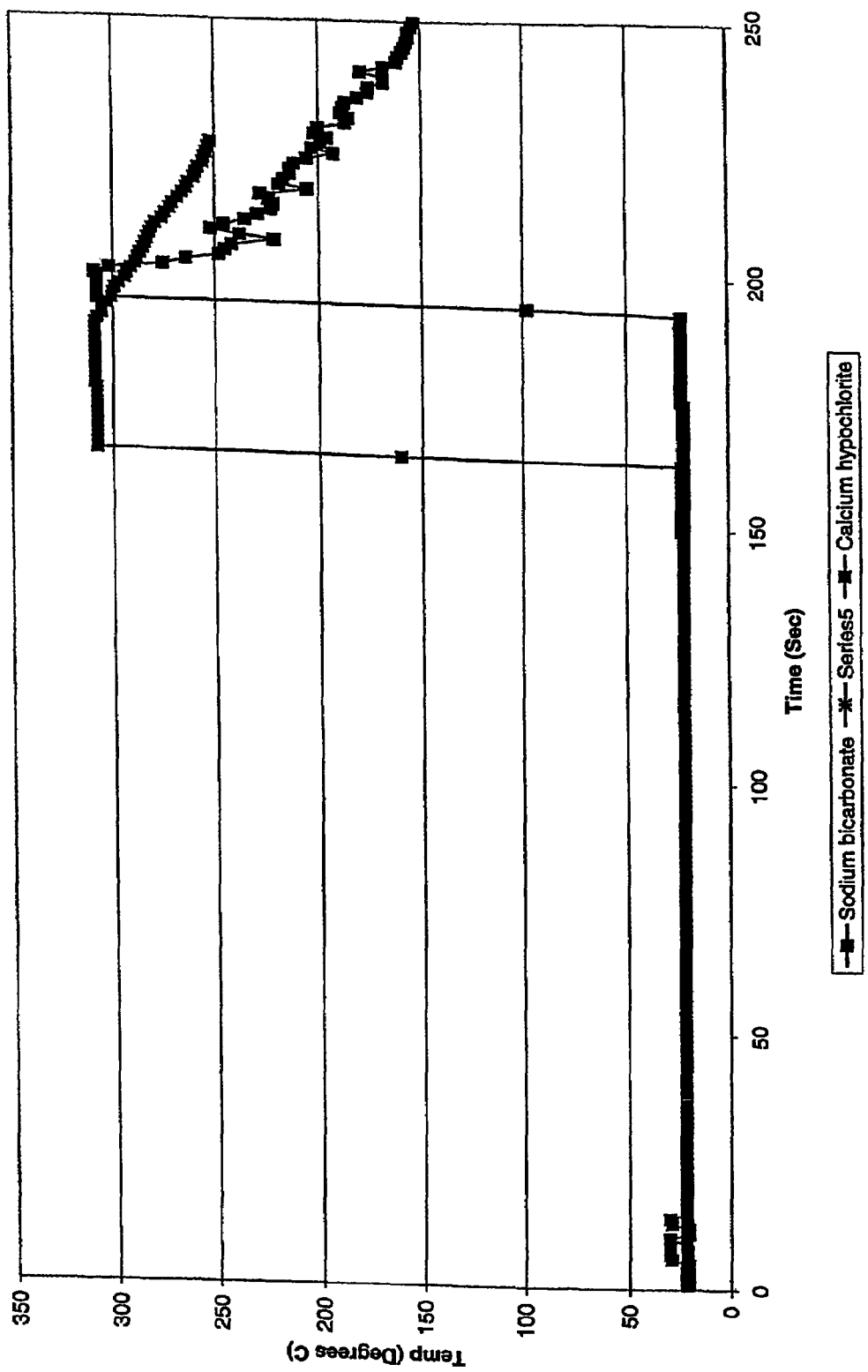
FIG. 3 is a chart of temperature over time of Calcium Hypochlorite and Brake Fluid Compared to a Blend of Calcium Hypochlorite and Sodium Bicarbonate and Brake Fluid.

Although inorganic salt hydrates release water to quench the reaction of cal hypo and brake fluid other inorganic compounds can also have an effect on this reaction. Boric acid decomposes when heated and releases water thus effectively reducing an exothermic reaction. A mixture of 30% sodium bicarbonate and 70% calcium hypochlorite decomposes when heated to release carbon dioxide thus reducing an exothermic reaction. This is illustrated in FIG. 3.

Based on the results of Examples 1-4, a range for the various inorganic salt hydrates can be specified. Stable formulations containing up to 30% each of 2 salt hydrates. The salt hydrates can be selected from the group consisting of magnesium sulfate heptahydrate, potassium aluminum sulfate dodecahydrate, trisodium phosphate dodecahydrate, sodium tripolyphosphate hexahydrate and sodium tetraborate decahydrate. More preferably compositions could contain from 0.1 to 19% magnesium sulfate heptahydrate, 0.1 to 19% potassium aluminum sulfate dodecahydrate, 0.1 to 19% trisodium phosphate dodecahydrate, 0.1 to 10% sodium tripolyphosphate hexahydrate, and 0.1 to 10% sodium tetraborate decahydrate.

Further variations and modifications of the foregoing will be apparent to those skilled in the art and are intended to be encompassed by the claims appended hereto.

I claim:

1. A hydrated calcium hypochlorite composition having reduced potential for conflagration made by a method comprising:
    a) selecting at least two hydrated inorganic salts from the group consisting of:
    magnesium sulfate heptahydrate in an amount ranging from 0.1. to 19% by weight,
    potassium aluminum sulfate dodecahydrate in an amount ranging from 0.1. to 19% by weight,
    trisodium phosphate dodecahydrate in an amount ranging from 0.1. to 19% by weight,
    sodium tripolyphosphate hexahydrate in an amount ranging from 0.1. to 10% by weight, and
    sodium tetraborate decahydrate in an amount ranging from 0.1. to 19% by weight,
    b) thereafter adding said at least two hydrated inorganic salts to at least 40% by weight of hydrated calcium hypochlorite to form a mixture,
    c) whereby said mixture provides water release in an endothermic reaction to sufficiently quench dangerous reactions and reduce potential for conflagration while providing increased chlorine stability as compared to hydrated calcium hypochlorite blends containing a single hydrated inorganic salt.

2. The composition according to claim 1 wherein said mixture comprises 70% hydrated calcium hypochlorite, 14.3% magnesium sulfate heptahydrate, 9% potassium aluminum sulfate dodecahydrate, 4.7% trisodium phosphate dodecahydrate and 2% sodium tripolyphosphate hexahydrate.

3. The composition according to claim 1 wherein the calcium hypochlorite contains from 5% to 22% water.

4. The composition according to claim 1 wherein said mixture is in granular form.

5. The composition according to claim 1 wherein the hydrated calcium hypochlorite contains at least 55% available chlorine.

6. The composition according to claim 1 wherein the hydrated calcium hypochlorite contains about 5.5% to 10% water.

7. The composition according to claim 1 wherein the hydrated calcium hypochlorite is present in the amount of 40% to 90% by weight.

8. The composition according to claim 7 wherein the hydrated calcium hypochlorite is present in an amount of about 50% to 85% by weight.

9. The composition according to claim 8 wherein the hydrated calcium hypochlorite is present in an amount of about 60% to 80% by weight.

* * * * *